United States Patent
Lin (10) Patent No.: US 6,700,663 B1
(45) Date of Patent: Mar. 2, 2004

(54) METHOD OF MONITORING A LASER CRYSTALLIZATION PROCESS

(75) Inventor: Kun-chih Lin, Hsin-Chu Hsien (TW)

(73) Assignee: AU Optronics Corp., Hsin-Chu (TW)

( * ) Notice: Subject to any disclaimer, the term of this patent is extended or adjusted under 35 U.S.C. 154(b) by 37 days.

(21) Appl. No.: 10/248,442

(22) Filed: Jan. 21, 2003

(30) Foreign Application Priority Data

Nov. 29, 2002 (TW) ........................................ 91134683 A (51) Int. Cl.[7] .................................................. G01J 4/00

(52) U.S. Cl. ........................................ 356/369; 356/364

(58) Field of Search ................................ 356/364–369, 356/237.1–237.5, 381, 382; 250/225

(56) References Cited

U.S. PATENT DOCUMENTS

| | | | | |
|---|---|---|---|---|
| 6,073,464 A | * | 6/2000 | Boher et al. | 65/378 |
| 6,128,084 A | * | 10/2000 | Nanbu et al. | 356/369 |
| 6,141,103 A | * | 10/2000 | Pinaton et al. | 356/369 |
| 2002/0145733 A1 | * | 10/2002 | Wada et al. | 356/237.2 |

\* cited by examiner

*Primary Examiner*—Michael P. Stafira
(74) *Attorney, Agent, or Firm*—Winston Hsu (57) ABSTRACT

An amorphous silicon thin film is formed on a substrate first. Then the thin film is irradiated by a laser plus having an irradiation interval along a first direction to re-crystallize the thin film into a polysilicon thin film. A light source is thereafter focused into a micro spot having a diameter smaller than the irradiation interval, and the polysilicon thin film is irradiated by the micro spot moving along the first direction and having a relative moving distance to obtain a spectrum.

18 Claims, 6 Drawing Sheets

METHOD OF MONITORING A LASER CRYSTALLIZATION PROCESS

BACKGROUND OF INVENTION

1. Field of the Invention

The present invention relates to a method of monitoring a laser crystallization (LC) process, and more particularly, to a method of on-line monitoring the result and the uniformity of the laser crystallization process quickly by utilizing a variable wavelength ellipsometry.

2. Description of the Prior Art

Nowadays, a liquid crystal display(LCD)is the most mature flat panel display technique. The applications for a liquid crystal display are extensive, such as mobile phones, digital cameras, video cameras, notebooks, and monitors. Due to the high quality vision requirements and the expansioninto new application fields, the LCD has developed toward high quality, high resolution, high brightness, and low price. A low temperature polysilicon thin film transistor (LTPS TFT), having a character of being actively driven, is a break-through in achieving the above objectives. Furthermore, a metal-oxide-semiconductor and the low temperature polysilicon thin film transistor in this technique are integrated in a same manufacturing process to fabricate a system on panel (SOP). The low temperature polysilicon thin film transistor therefore has become a booming development area for all of the vendors.

During the manufacturing process of the low temperature polysilicon thin film transistor liquid crystal display, a glass substrate tends to deform if the polysilicon film is directly formed at a high temperature since the resistance of the glass substrate to heat is merely up to 600° C. As a result, an expensive quartz is utilized as the substrate for the traditional polysilicon thin film transistor liquid crystal display. The application is therefore limited to small sized liquid crystal display panels. Nowadays, a method to re-crystallize the amorphous silicon thin film has come with the tide of fashion and has become main stream. More particularly, the excimer laser annealing (ELA) process is most significant.

Figure 1:
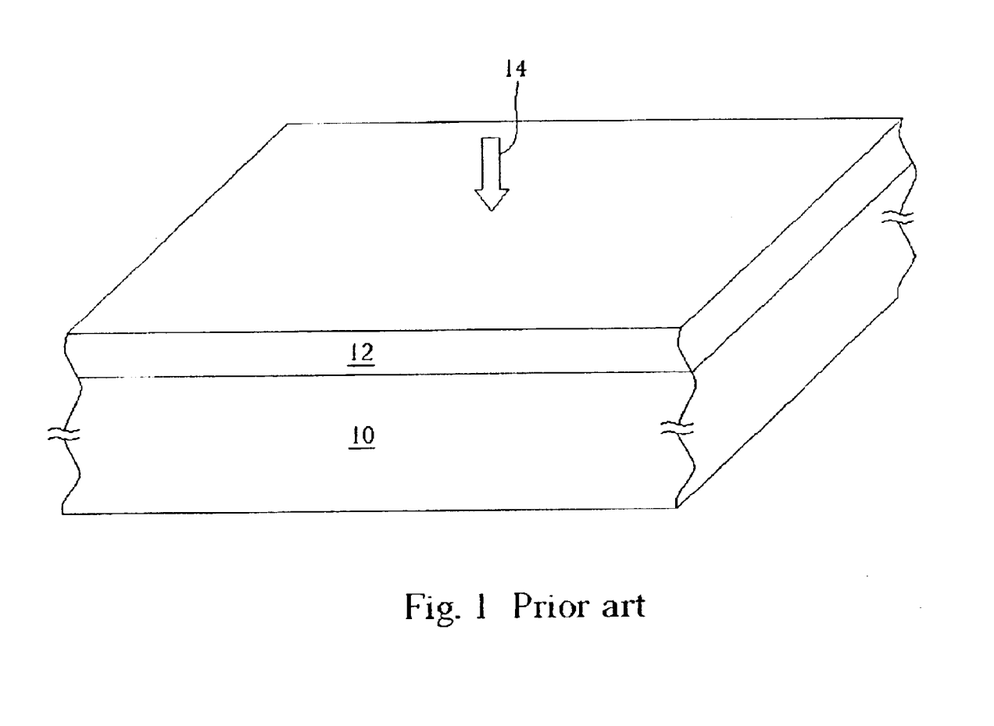
FIG. 1 is a schematic diagram of a method of forming a polysilicon thin film by utilizing an excimer laser annealing process.

Please refer to FIG. 1. FIG. 1 is a schematic diagram of a method of forming a polysilicon thin film by utilizing an excimer laser annealing process. As shown in FIG. 1, an amorphous silicon thin film 12 having a thickness of approximate 500 Å is deposited on a glass substrate 10 first. Then the glass substrate 10 is disposed in a hermetic chamber (not shown) to perform the excimer laser annealing process. The method for depositing the amorphous silicon thin film 12 comprises a low-pressure chemical vapor deposition (LPCVD) process, a plasma enhanced chemical vapor deposition (PECVD) process, or a sputtering process. When performing the excimer laser annealing process, the amorphous silicon thin film 12 on the surface of the glass substrate 10 is irradiated by the laser pulse 14 of the excimer laser through a transparent window (not shown) on the upper surface of the chamber (not shown). The laser pulse 14 scans the regions within a process scope, which is determined previously, step-by-step to heat the amorphous silicon thin film 12 within the process scope rapidly. The amorphous silicon thin film 12 is therefore re-crystallized into a polysilicon thin film (not shown).

Moreover, the amorphous silicon thin film is melted and re-crystallized rapidly through absorption of the deep ultraviolet light during the excimer laser annealing process to form the polysilicon thin film. Such a quick absorption due to the short laser pulse only affects the surface of the amorphous silicon thin film and will not affect the glass substrate. Hence, the glass substrate is kept in a low temperature state. The excimer lasers frequently used comprise a XeCl laser, an ArF laser, a KrF laser, and a XeF laser. Since the different molecules will generate light with different wavelengths, the out energy density is therefore adjusted according to the thickness of the amorphous silicon thin film. For example, the output energy density is approximately 200 to 400 mJ/cm$^2$ for an amorphous silicon thin film with a thickness of 500 Å. After performing the excimer laser annealing process, the subsequent processes for forming the liquid crystal display panel are performed. The polysilicon thin film is used as a channel or a source/drain to form the driving circuit or the logic circuit on the liquid crystal display panel.

Since the quality of the amorphous silicon thin film 12 is a determinative factor for the characteristics of the subsequently formed polysilicon thin film, all of the parameters during the amorphous silicon thin film deposition process need to be strictly controlled. The amorphous silicon thin film with low hydrogen content, high thickness uniformity and low surface roughness is thus formed. In addition, many variables during the crystallization process, such as the magnitude of the laser energy density, the spatial uniformity of the laser energy, the overlapping ratio of the laser pulse, the substrate temperature during the laser annealing process and the atmosphere, will directly affect the grain size and the grain distribution after the crystallization process is completed. When non-uniform phenomenon occurs during the crystallization process, a strip type defect emerges.

In view of this, an inspection process is usually performed to monitor the result and the uniformity of the laser crystallization process. The method utilized in the inspection process usually comprises a visual inspection method, a scanning electron microscope (SEM) observation method, or a spreading resistance measurement (SR measurement) method.

However, all of the prior art methods of monitoring the laser crystallization process have drawbacks. The visual inspection method can't provide an objective result. Moreover, when the dimensions of the substrate become larger and larger, the visual inspection method is not applicable. The method utilizing the scanning electron microscope to observe the grain microstructure is a destructive inspection method. Both the sample preparation and the sample observation take lots of time. Therefore, this method is not timely at all. In addition, the crystallization uniformity can't be judged definitely by this method. The spreading resistance measurement method is also a destructive inspection method. In order to increase the film conductivity, dopants need to be doped into the sample and activated. The measurement result is readily affected by the doping uniformity and the activating uniformity.

Therefore, it is very important to develop a method of monitoring the laser crystallization process. This method should not only be a non-destructive inspection method, but is also applicable to a substrate of any size. Furthermore, this method should reflect the result and the uniformity of the crystallization process rapidly and definitely in the on-line circumstance.

SUMMARY OF INVENTION

It is thereforean object of the claimed invention to provide a method of monitoring the laser crystallization (LC) process, especially a method of on-line monitoring the result and the uniformity of the laser crystallization process quickly by utilizing a variable wavelength ellipsometry.

According to the claimed invention, a substrate is provided first. Then an amorphous silicon thin film is formed on a surface of the substrate. A laser crystallization process is thereafter performed to re-crystallize the amorphous silicon thin film into a polysilicon thin film by irradiating the amorphous silicon thin film with a laser pulse along a first direction. The laser pulse has an irradiation interval. After that, a light source provided by an optical instrument is focused into a micro spot with a diameter. The polysilicon thin film is irradiated by the micro spot along the first direction to obtain at least one measured spectrum. The micro spot has a moving distance relative to the substrate. Finally, a comparison step is performed to compare each measured spectrum with a pre-set spectrum. The diameter of the micro spot is smaller than the irradiation interval, the moving distance of the micro spot relative to the substrate is smaller than the irradiation interval.

The method of monitoring the laser crystallization process is to utilize a variable wavelength ellipsometry, which is employed in the production line, to focus the light source into a micro spot having a diameter smaller than the irradiation interval. The moving distance of the micro spot relative to the substrate is also smaller than the irradiation interval too. A non-destructive inspection is thus performed to the polysilicon film. As a result, the present invention method effectively avoids the not reflected strip type defect problem due to one of the irradiation intervals of the laser pulse being unsampled. The present invention method is suitable and convenient for on-line application. In addition, the present invention method is applicable to the substrate of any size to rapidly and definitely reflect the result and the uniformity of the crystallization process.

These and other objectives of the claimed invention will no doubt become obvious to those of ordinary skill in the art after having read the following detailed description of the preferred embodiment that is illustrated in the various figures and drawings.

BRIEF DESCRIPTION OF DRAWINGS

FIG. 2 to FIG. 5 are schematic diagrams of a method of forming and monitoring a polysilicon thin film by utilizing an excimer laser annealing process according to the present invention.

DETAILED DESCRIPTION

Figure 2:
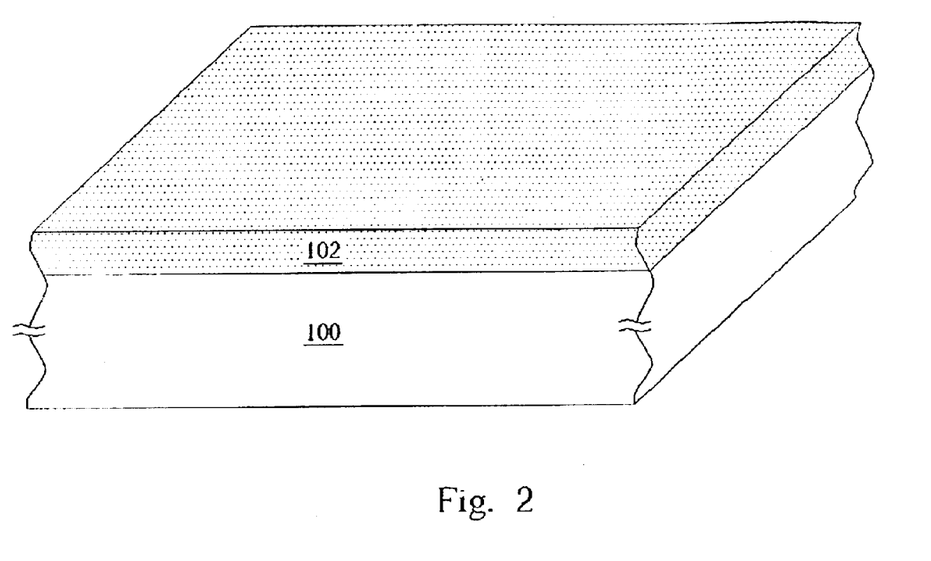

Please refer to FIG. 2 to FIG. 5 that are schematic diagrams of a method of forming and monitoring a polysilicon thin film 116 by utilizing an excimer laser annealing process according to the present invention. As shown in FIG. 2, an amorphous silicon thin film 102 having a thickness of approximate 500 Å is deposited on an insulation substrate 100 first. The insulation substrate 100 is a glass substrate, a quartz substrate, or a plastic substrate. The method for depositing the amorphous silicon thin film 102 comprises a low pressure chemical vapor deposition (LPCVD) process, a plasma enhanced chemical vapor deposition (PECVD) process, or a sputtering process. After forming the amorphous silicon thin film 102, a photo-etching-process (PEP) may be performed, according to the design of the device or the requirements of a subsequent process, to pattern the amorphous silicon thin film 102 into an amorphous silicon pattern (not shown).

Figure 3:
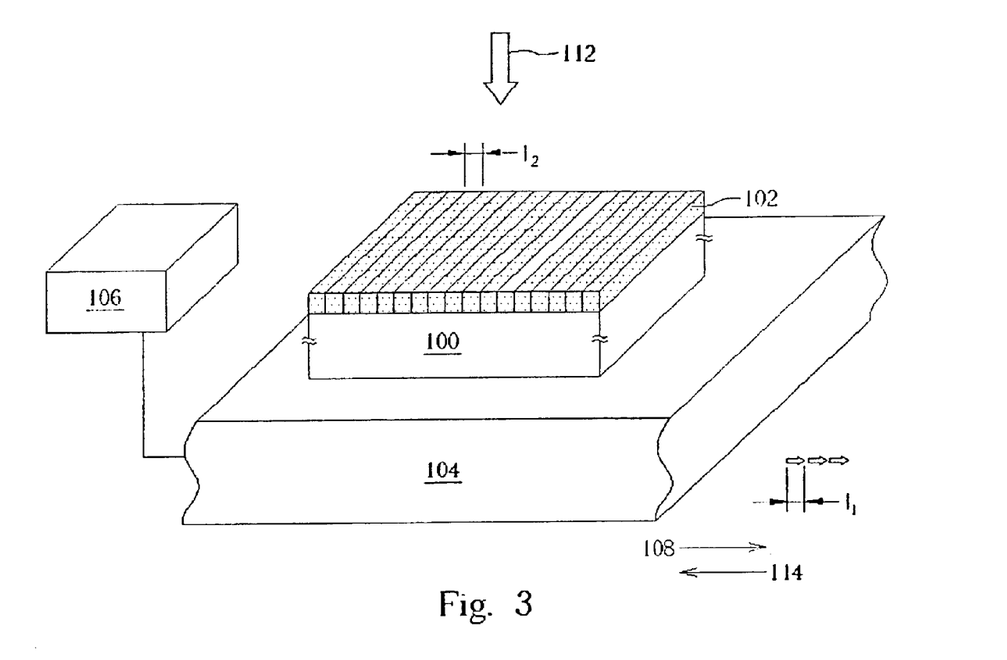

As shown in FIG. 3, the insulation substrate 100 is thereafter disposed in a hermetic chamber (not shown) to perform the excimer laser annealing process. When performing the excimer laser annealing process, the amorphous silicon thin film 102 on the surface of the insulation substrate 100 is irradiated by the excimer laser through a transparent window (not shown) on the upper surface of the chamber (not shown). The excimer laser comprises a XeCl laser, an ArF laser, a KrF laser, or a XeF laser. Different molecules will generate light with different wavelengths.

When performing the excimer laser annealing process, the insulation substrate 100 is disposed on a carrier stage 104. The carrier stage 104, driven by a moving apparatus 106, moves along a first direction 108. Since the carrier stage 104 has a moving interval $I_1$, identically the amorphous silicon thin film 102 is irradiated by a site fixed laser pulse 112 along a second direction 114 (the direction opposite to the first direction) to re-crystallize the amorphous silicon thin film 102 into a polysilicon thin film (not shown). The laser pulse 112 has an irradiation interval $I_2$, the irradiation interval $I_2$ is equal to the moving interval $I_1$.

Of course, the laser pulse 112 may be scanned in a predetermined process scope. Furthermore, the irradiation interval $I_2$ of the laser pulse 112 results in a specific overlapping ratio, which is usually 90% or 95%. When the laser pulse 112 scans the amorphous silicon thin film 102 step-by-step, the amorphous silicon thin film 102 is rapidly heated to re-crystallize into a polysilicon thin film (not shown).

Figure 4A:
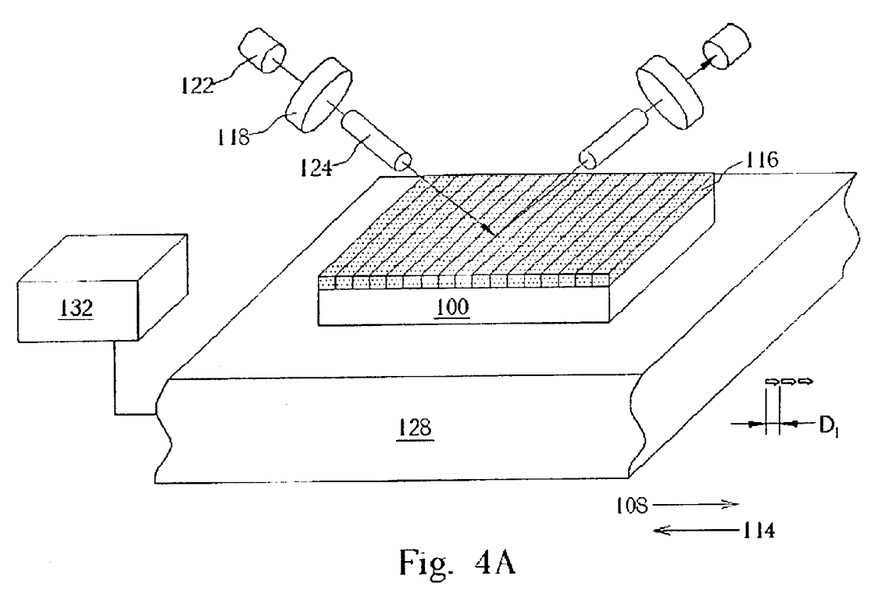
Figure 4B:
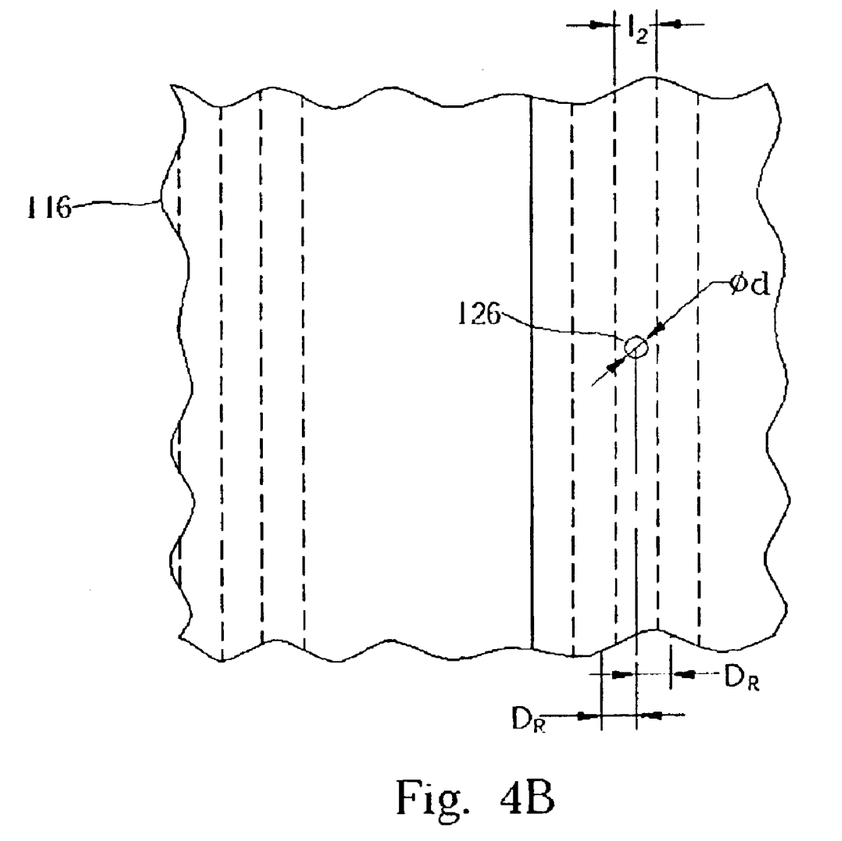

As shown in FIG. 4a and FIG. 4B, a variable wavelength ellipsometry (not shown) is then utilized to inspect the as formed polysilicon thin film 116. A polarizer 118 is utilized to polarize a light source 122 provided by the variable wavelength ellipsometry (not shown), to form a polarized light first. A micro tube 124 thereafter focuses the polarized light into a micro spot 126 having a diameter d. The diameter d of the micro spot 126 is smaller than the irradiation interval $I_2$.

When performing the inspection, the insulation substrate 100 is disposed on a carrier stage 128. The carrier stage 128, driven by a moving apparatus 132, moves along a first direction 108. Since the carrier stage 128 has a moving distance $D_1$, identically the site fixed micro spot 126 has a moving distance $D_R$ relative to the insulation substrate 100.

The moving distance $D_1$ is equal to the relative moving distance $D_R$. The relative moving distance $D_R$ could be a positive distance or a negative distance, and the relative moving distance $D_R$ is smaller than the irradiation interval $I_2$. In other words, the micro spot 126 irradiates the polysilicon thin film 116 along the second direction 114 (the direction opposite to the first direction) or the first direction to sample the polysilicon thin film 116. The measured spectrum for each sample is thus obtained. Since the diameter d of the micro spot 126 is smaller than the irradiation interval $I_2$ and the relative moving distance $D_R$ of the micro spot 126 is smaller than the irradiation interval $I_2$ none of the irradiationintervals of the laser pulse are unsampled. Hence, there is no such a consideration that the strip type defect is not detected.

The sampling site and the sampling quantities are determined according to the practical requirements. The inspected substrate may be either a product or a testing substrate. As previously mentioned, if a photo-etching-process (PEP) is comprised after forming the amorphous silicon thin film to pattern the amorphous silicon thin film into an amorphous silicon pattern, the micro spot 126 is irradiated on the polysilicon thin film 116 in a testing area (not shown) on the substrate to obtain the measured spectrum.

Figure 5:
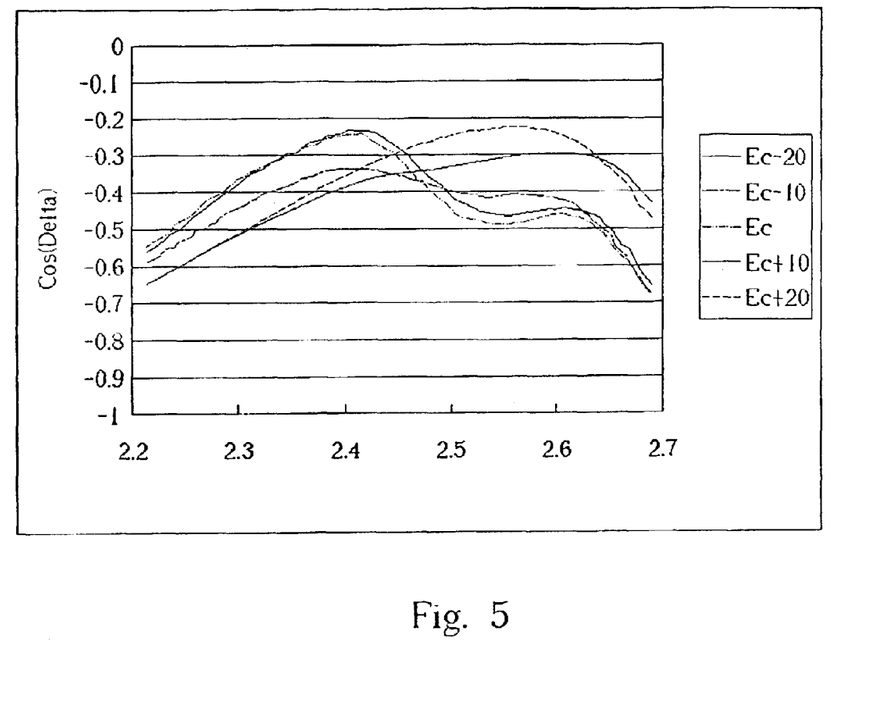

As shown in FIG. 5, the measured spectrum is a Cos (Delta)-photon energy continuous spectrum (Cos δ-photon energy continuous spectrum). In FIG. 5, it is obvious that the spectrum obtained from the crystallization process of the amorphous silicon thin film 102 proceeded at the optimum crystallization energy density (Ec) is different from yet similar to the spectrum obtained from the crystallization process of the amorphous silicon thin film 102 proceeded at the acceptable crystallization energy density (Ec±10cm$^2$). These three spectra are different from the spectrum obtained from the crystallization process of the amorphous silicon thin film 102 proceeded at the not acceptable crystallization energy density (Ec±20cm$^2$).

Therefore, a pre-set spectrum representing the spec for the laser crystallization process may be established on-line first. After that, a comparison step is performed after the inspection process to compare each measured spectrum with the pre-set spectrum. When the measured spectrum is out of spec, the laser crystallization process is not acceptable. The laser crystallization process is thus monitored. It is worth noticing an external charge-coupled device camera (CCD camera) may be utilized to gather a microstructure image for the polysilicon thin film in the present invention. In this case, the microstructure image is used for judging if the laser crystallization process is acceptable or not.

The method of monitoring the laser crystallization process according to the present invention is to utilize a variable wavelength ellipsometry to focus the light source into a micro spot. The diameter d of the micro spot is smaller than the irradiation interval and the moving distance of the micro spot relative to the substrate is smaller than the irradiation interval. By utilizing this method to inspect the polysilicon thin film, not only the destruction will not occur, but also none of the irradiation intervals of the laser pulse are unsampled, avoiding the not reflected strip type defect problem. Furthermore, the present invention method is applicable to the substrate of any size in a practical production line to rapidly and definitely reflect the result and the uniformity of the crystallization process. The present invention method is able to effectively monitor the yield for the laser crystallization process to reduce the failure cost when either inspecting the testing substrate before production or inspecting the product or the testing substrate after production.

In comparison with the prior art method of monitoring the laser crystallization process, the present invention method utilizes a variable wavelength ellipsometry, which is employed in the production line, to focus the light source into a micro spot having a diameter smaller than the irradiation interval. The moving distance of the micro spot relative to the substrate is also smaller than the irradiation interval. By correlating the measured spectrum to the crystallization characteristics of the polysilicon thin film and by performing a comparison step, a non-destructive inspection is performed to the polysilicon film in the present invention method. Therefore, none of the irradiation intervals of the laser pulse are unsampled, avoiding the not reflected strip type defect problem. The present invention method is suitable and convenient for on-line application. Furthermore, the present invention method is applicable to the substrate of any size to rapidly and definitely reflect the result and the uniformity of the crystallization process.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of monitoring a laser crystallization (LC) process by utilizing an optical instrument, the method comprising the steps of:

providing a substrate, a polysilicon thin film formed by the laser crystallization process being formed on a surface of the substrate;

focusing a light source provided by the optical instrument into a micro spot with a diameter, the polysilicon thin film being irradiated by the micro spot along a first direction to obtain at least one measured spectrum, the micro spot having a relative moving distance to the substrate; and performing a comparison step to compare the measured spectrum with a pre-set spectrum;

wherein the diameter of the micro spot is smaller than an irradiation interval, the relative moving distance of the micro spot to the substrate is smaller than the irradiation interval.

2. The method of claim 1 wherein the substrate comprises a glass substrate, a quartz substrate, or a plastic substrate.

3. The method of claim 1 wherein the laser is an excimer laser (EL).

4. The method of claim 3 wherein the excimer laser comprises a XeCl laser, an ArF laser, a KrF laser, or a XeF laser.

5. The method of claim 1 wherein the method for forming the polysilicon thin film further comprises the following steps:

forming an amorphous silicon thin film (α-Si thin film) on the surface of the substrate; and performing the laser crystallization process to irradiate the amorphous silicon thin film along the first direction to re-crystallize the amorphous silicon thin film into the polysilicon thin film by utilizing a laser pulse having the irradiation interval.

6. The method of claim 5 wherein the method for forming the amorphous silicon thin film comprises a low-pressure chemical vapor deposition (LPCVD) process, a plasma enhanced chemical vapor deposition (PECVD) process, or a sputtering process.

7. The method of claim 5 wherein a photo-etching-process (PEP) is comprised after forming the amorphous silicon thin film to pattern the amorphous silicon thin film into an amorphous silicon pattern.

8. The method of claim 7 wherein the micro spot is irradiated on the polysilicon thin film in a testing area on the substrate to obtain the measured spectrum.

9. The method of claim 5 wherein the method of irradiating the amorphous silicon thin film by utilizing the laser pulse further comprises the following steps:

disposing the substrate on a carrier stage; and moving the carrier stage along the direction opposite to the first direction by utilizing a moving apparatus, an moving interval of the carrier stage is equal to the irradiation interval.

10. The method of claim 5 wherein the irradiation interval of the laser pulse results in an overlapping ratio more than 90%.

11. The method of claim 1 wherein the optical instrument is a variable wavelength ellipsometry.

12. The method of claim 11 wherein the method of focusing the light source into the micro spot with the diameter further comprises the following steps:

polarizing the light source to form a polarized light by utilizing a polarizer; and focusing the polarized light into the micro spot with the diameter by utilizing a micro tube.

13. The method of claim 11 wherein the measured spectrum is a Cos(Delta)-photon energy continuous spectrum (Cosδ-photon energy continuous spectrum), the Cos(Delta)-photon energy continuous spectrum is compared with the established pre-set spectrum representing the spec for the laser crystallization process to monitor the laser crystallization process.

14. The method of claim 13 wherein the laser crystallization process is not acceptable when the measured spectrum is out of spec.

15. The method claim 1 wherein the method of irradiating the pollysilicon thin film along the first direction by utilizing the micro spot having the relative moving distance to the substrate further comprises the following steps:

disposing the substrate on a carrier stage; and moving the carrier stage along the first direction by utilizing a moving apparatus, a moving distance of the carrier stage is equal to the relative moving distance.

16. The method of claim 1 wherein the relative moving distance comprises a positive distance or a negative distance.

17. The method of claim 1 wherein the diameter of the micro spot is smaller than the irradiation interval and the relative moving distance of the micro spot to the substrate is smaller than the irradiation interval is used to avoid the irradiation interval of the laser pulse unable to be sampled.

18. The method of claim 1 wherein the optical instrument further comprises an external charge-coupled device camera (CCD camera) to gather the microstructure image for the polysilicon thin film.

* * * * *